United States Patent
Chen

(10) Patent No.: US 7,550,468 B2
(45) Date of Patent: Jun. 23, 2009

(54) THEOPHYLLINE AND 3-ISOBUTYL-1 METHYLXANTHINE BASED N-7 SUBSTITUTED DERIVATIVES DISPLAYING INHIBITORY ACTIVITIES ON PDE-5 PHOSPODIESTERASE

(76) Inventor: Ing-Jun Chen, 10F, No. 148-95, Guang-Hwa 1$^{st}$ Rd., Kaohsiung (TW)

( * ) Notice: Subject to any disclaimer, the term of this patent is extended or adjusted under 35 U.S.C. 154(b) by 431 days.

(21) Appl. No.: 11/122,343

(22) Filed: May 4, 2005

(65) Prior Publication Data

US 2005/0209242 A1 Sep. 22, 2005

Related U.S. Application Data

(63) Continuation-in-part of application No. 10/342,650, filed on Jan. 15, 2003, now abandoned, which is a continuation-in-part of application No. 09/906,245, filed on Jul. 16, 2001, now abandoned.

(30) Foreign Application Priority Data

Jul. 28, 2000 (TW) ............................... 89115304 A

(51) Int. Cl.
C07D 473/08 (2006.01)
C07D 473/06 (2006.01)
A61K 31/522 (2006.01)

(52) U.S. Cl. .................. 514/252.16; 544/267; 544/269; 544/270; 544/271; 544/273

(58) Field of Classification Search ............... 514/263.2, 514/263.21, 263.22, 263.23, 263.34, 263.35, 514/263.36, 252.16; 544/267, 269, 270, 544/271, 272, 273

See application file for complete search history.

(56) References Cited

U.S. PATENT DOCUMENTS

| | | | | |
|---|---|---|---|---|
| 4,284,633 A | * | 8/1981 | Friebe et al. | 514/265 |
| 4,299,832 A | * | 11/1981 | Brown et al. | 514/263 |
| 4,599,414 A | * | 7/1986 | Sugimoto et al. | 544/267 |
| 2005/0209243 A1 | * | 9/2005 | Chen | 514/252.16 |
| 2008/0064705 A1 | * | 3/2008 | Chen | 514/252.16 |

OTHER PUBLICATIONS

Daly, Journal of Medicinal Chemistry (1986), 29(7), 1305-8.*

* cited by examiner

*Primary Examiner*—Mark L Berch
(74) *Attorney, Agent, or Firm*—Stephen M. Nipper; Dykas, Shaver & Nipper, LLP

(57) ABSTRACT

A variety of N-substituted derivatives are based upon the base chemicals of

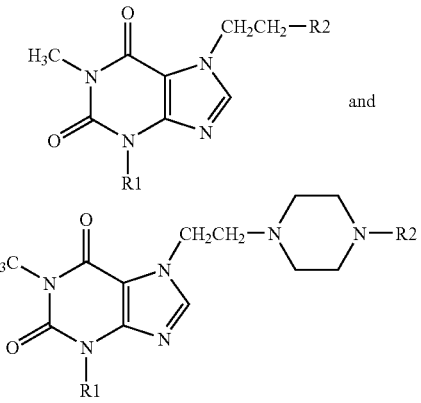

that provide for the induction of cavernosal relaxation in animals. R2 is a derivative based on a hetroaromatic group, an aromatic group or a cyclohexane.

7 Claims, 6 Drawing Sheets

R =CH$_2$CH(CH$_3$)$_2$ or R$_1$ =CH$_3$

THEOPHYLLINE AND 3-ISOBUTYL-1 METHYLXANTHINE BASED N-7 SUBSTITUTED DERIVATIVES DISPLAYING INHIBITORY ACTIVITIES ON PDE-5 PHOSPODIESTERASE

PRIORITY

This application claims priority from and is a Continuation-in-Part of U.S. application Ser. No. 10/342,650 filed by Ing Jun Chen on Jan. 15, 2003 now abandoned which is a Continuation-in-Part of U.S. application Ser. No. 09/906,245 filed by Ing Jun Chen on Jul. 16, 2001, now abandoned the contents of which are herein incorporated by reference.

BACKGROUND OF THE INVENTION

1. Field of the Invention

This present invention generally relates to compounds of Theophylline and 3-Isobutyl-1-methylxanthine (IBMX) having N-7 substituted derivatives, and more particularly to the compounds and use of such compounds in various pharmacological applications.

2. Background Information

The endothelium plays a major role in regulating vascular smooth muscle (VSM) tone through the release of a variety of vasoactive factors. Among the endothelium-derived vasodilators, nitric-oxide (NO) is probably the primary mediator of endothelium-dependent relaxation in most blood vessels. Nitric Oxide in numerous bioregulatory pathways has not only expanded new therapeutic related compounds but has also led to an increased use of such compounds in pharmacological studies.

In recent years, the nitric oxide gas has been shown to be an important regulator of vascular functions by controlling blood vessel tone as well as blood cell interactions with the vascular wall. (S. Moncada et al., Pharmacol. Rev. vol. 43, No. 2, pp. 109-142, 1991). The action of NO (Nitric Oxide) as a vasodilator is mediated by the activation of vascular smooth muscle soluble guanylyn cyclase (sCG), a signal tranduction enzyme which forms the second messenger of molecular cyclic GMP (William P. Arnold et al., Proc. Natl Acad Sci. vol. 74 No. 8 pp. 3203-3207, 1977 Charles J. Lowenstein et al. Ann. Intern. Med. Vol 102, No. 3 pp. 227-237, 1994). The activity of several cyclic GMP (guanosine 3'5'-cyclic monophosphate) which lead to vasorelaxation has been determined. The membrane-bound guanylyl cyclases are receptor-like enzymes which are activated by extracellular binding of natriuretic peptides. In contrast, soluble guanylyl cyclases act via their hemoglobin group which is an important intracellular receptor for nitric oxide. (Paulus Wohlfart et al Br. J. Pharmcol. Vol. 128, pp. 1316-1322, 1999) Moreover, the increases in cGMP with these guanylyl cyclase activators and phosphodiesterases (PDE) or cGMP breakdown inhibition which have been associated with the relaxation of vascular and tracheal smooth muscles.

These interactions between endogenous NO or NO donors and endothelium-derived hyperpolarizing factor (EDHF) or K+ channels have received a great deal of attention. (Fransisco Perez Viscaino, et al. Brisitsh J. Pharmacol. Vol. 123, pp. 847-854, 1998). K+ channels play a major role in the regulation of the resting membrane potential and modulate VSM (vascular smooth muscle) tone. (Mark T. Nelson & John M. Quayle, Am. J. Physiol. vol 268, C799-C822, 1995). The endothelium-derived hyperpolarizing factor activates the potassium channels, and the potassium flux hyperpolarizes and thus relaxes the smooth muscle cell. Recent findings suggest that activation of endothelium $K_{ATP}$ channels (ATP-sensitive potassium channels) may also release endothelium-derived nitric oxide (Ethel C. Feleder & Edda Adler-Graschinsky Eur. J. pharmacol. Vol. 319 pp. 229-238, 1997) or endothelium-derived hyperpolarizing factor (Richard White and C. Robin Hiley, Eur. J. Pharmacol. Vol. 339, p157-160 1997). Nitric oxide donors have been shown to activate $K_{ATP}$ channels via a cyclic GMP-dependent mechanism, presumably involving activation of cyclic GMP-dependent protein kinase in rat aortic smooth muscle cells (Masahiro Kubo et al., Circ. Res. Vol. 74 No. 3 pp. 471-476, 1993) and rabbit mesenteric artery (Michael E. Murphy & Joseph E. Brayden, J. Physiol. Vol. 486, No. 1 pp. 47-48, 1995) and by a cyclic GMP-independent mechanism in the rat mesenteric artery. (Thomas Weidelt et al., J. Physiol. Vol. 500, No. 3 pp. 617-630, 1997) Although most of the endothelium-dependent relaxation is due to NO (nitric oxide), hyperpolarization associated with the K+ channels opening can supplement 60-80% of this response if no synthesis is blocked. (E. V. Kilpatrick & T. M. Cocks Br. J. Pharmacol. vol. 112 pp. 557-565, 1994)

The combination activity of soluble guanylyl cyclase (sGC) stimulation and K+ channels opening in a molecule such as that found in nicorandil, although shown without phosphodiesterase (PDE) inhibition activity, is able to relax agonist-induced vasoconstriction more fully. (F. Perez-Vizcaino et al. Br, J. Pharmacol. vol. 123, pp. 847-854, 1998) YC-1(3-(5'-hydroxymethyl-2-furyl)-1-benzyl-indazole) is representative of a class of sGC activator with PDE (phosphodiesterase) inhibition and leads to a long-lasting cyclic GMP-mediated inhibition of vasoconstriction (Jan Gaile et al., Br. J. Pharmacol. vol 127, pp 195-203, 1999).

The present invention includes various theophylline and 3-isobutyl-1-methylxanthine (IBMX) compounds having N-7 derivatives. In laboratory testing on animals, these compounds have been shown to possess desired inhibitory activities on PDE-5 Phosphodiesterase.

Additional objects, advantages and novel features of the invention will be set forth in part in the description which follows and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

This invention discloses theophylline (1-methyl-3-methylxanthine) and 1-methyl-3-isobutyl-xanthine (IMX) derivatives containing the theophylline moiety of formula I:

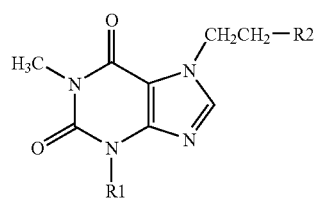

wherein R1 is —$(CH_2)_cCH_3$; and R2 is a member selected from the group consisting of the following moieties:

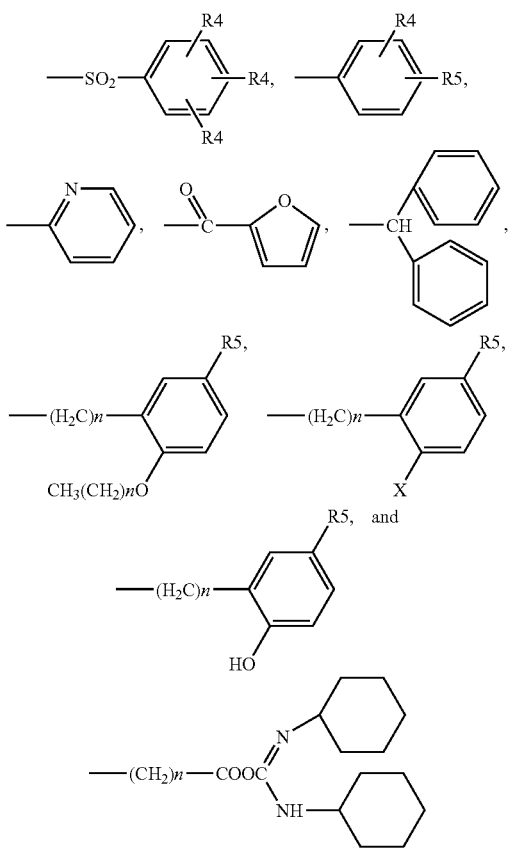

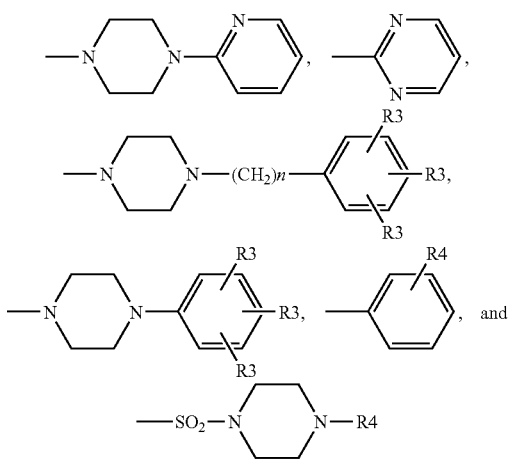

wherein $R_4$ is a member selected from the group of H, —$(CH_2)_nCH_3$, X, —$NH_2$, and —$NO_2$, wherein X is selected from the group consisting of F, Cl, Br, and I;

c is an integer from 0 to 3;

n is an integer from 0 to 3;

$R_5$ is a member selected from H, and the group consisting of wherein $R_3$ is a member selected from the group of halogen, hydroxyl group, a saturated straight chain alkyl group of 1-3 carbon atoms and a hydrogen atom. Preferably, $R_3$ is H, and n is between 1 and 3. These compounds of formula I provide for the induction of cavernosal relaxation.

It is another object of the present invention to provide a compound containing the theophylline moiety of formula II

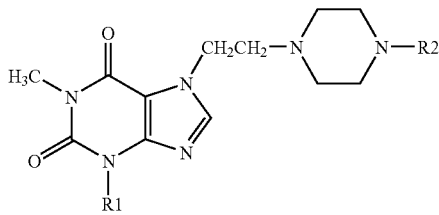

wherein $R_1$ is —$(CH_2)cCH_3$; $R_2$ is a member of the group selected from the group of:

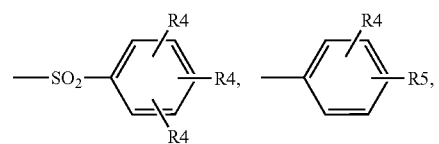

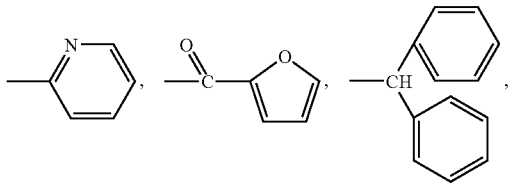

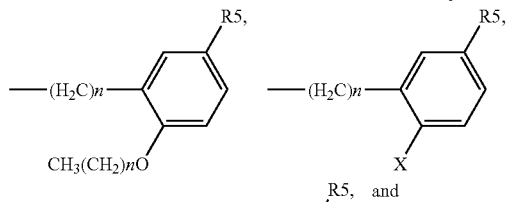

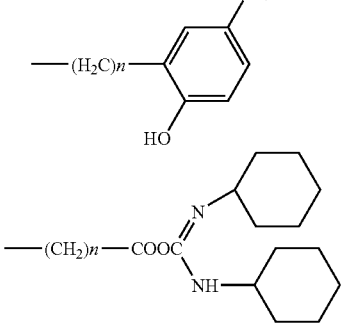

wherein $R_4$ is a member selected from the group of H, —$(CH_2)_nCH_3$, X, —$NH_2$, and —$NO_2$, wherein X is selected from the group of F, Cl, Br, or I.;

c is an integer from 0 to 3;

n is an integer from 0 to 3;

$R_5$ is a member selected from H, and the group of

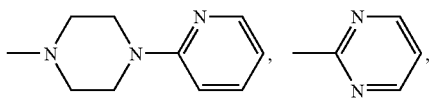

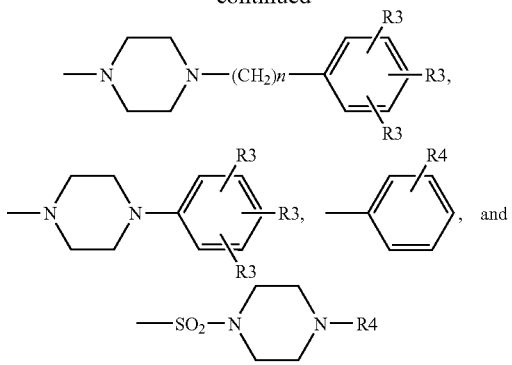

wherein $R_3$ is a member selected from the group of halogen, hydroxyl group, a saturated straight chain alkyl group of 1-3 carbon atoms and a hydrogen atom. Preferably, $R_3$ is H, and n is between 1 and 3. These compounds provide for the induction of cavernosal relaxation.

It is another object of the present invention to provide a process for the preparation of a compound of formula I

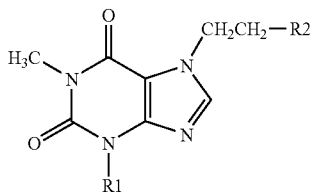

which comprises steps of (A) reacting of a compound of formula III

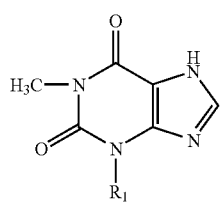

with 1,2-di-bromoethane as shown in reaction a

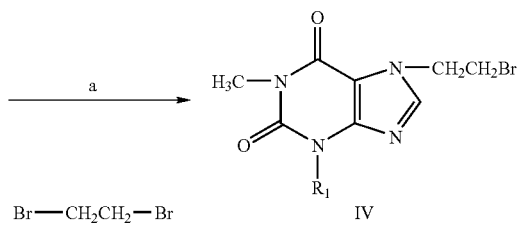

to produce a monobromo compound of formula IV, (B) reacting said monobromo compound of formula IV with the piperazinyl ring which is a secondary amine, (C) adding NaOH to precipitate NaBr, and (D) obtaining the product which contains the piperazinyl ring of formula I, wherein R1 is —$(CH_2)_c CH_3$; and R2 is a member selected from the group of the following moieties:

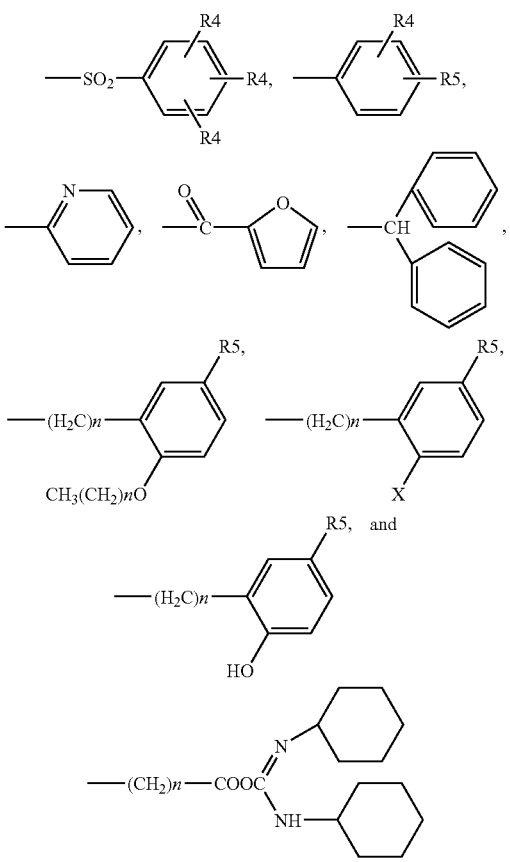

wherein $R_4$ is a member selected from the group of H, —$(CH_2)_n CH_3$, X, —$NH_2$, and —$NO_2$, wherein X is selected from the group of F, Cl, Br, or I;

c is an integer from 0 to 3;

n is an integer from 0 to 3;

$R_5$ is a member selected from H, and the group of

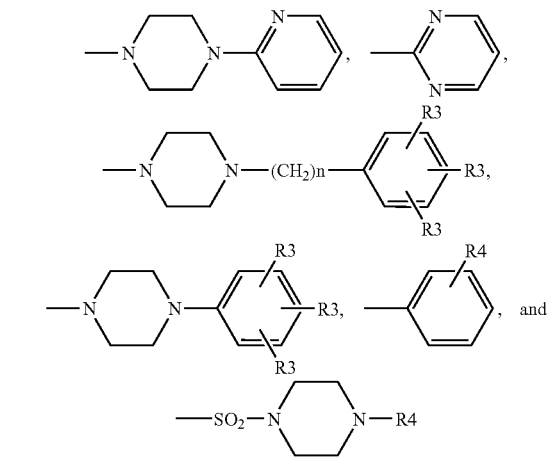

wherein $R_3$ is a member selected from the group of halogen, hydroxyl group, a saturated straight chain alkyl group of 1-3 carbon atoms and a hydrogen atom.

It is another object of the present invention to provide a first embodiment of a process for the preparation of a compound of formula II which comprises steps of (a) reacting of a compound of formula III

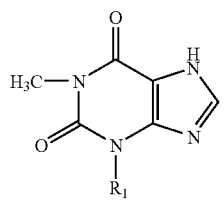

III with 1,2-di-bromoethane to produce a monobromo compound of formula IV according to reaction a

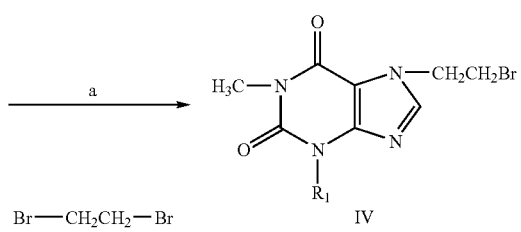

and (b) reacting said monobromo compound of formula IV with a N-substituted piperazine of formula piperazinyl-R2 according to reaction b to produce a compound of formula II

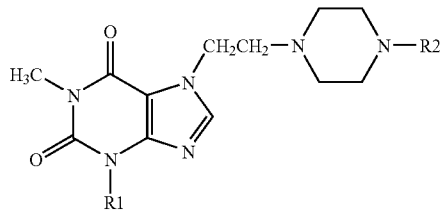

II wherein $R_1$ is —$(CH_2)cCH_3$; $R_2$ is a member of the group selected from the group of

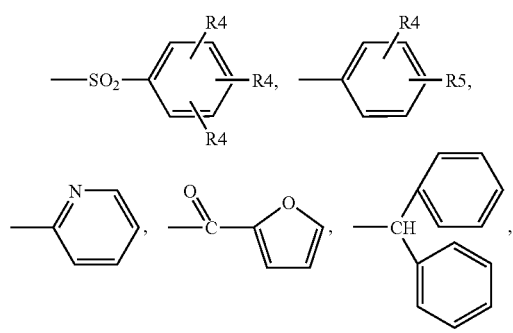

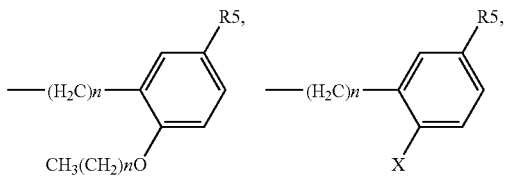

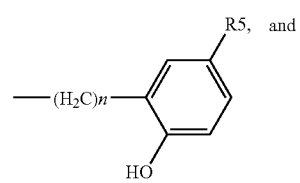

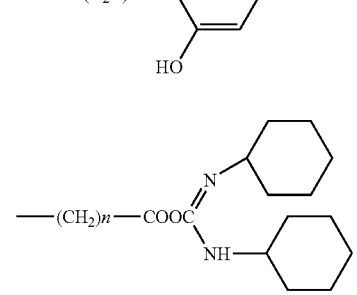

wherein $R_4$ is a member selected from the group of H, —$(CH_2)_nCH_3$, X, —$NH_2$, and —$NO_2$, wherein X is selected from the group of F, Cl, Br, or I, c is an integer from 0 to 3;

n is an integer from 0 to 3;

$R_5$ is a member selected from H, and the group of

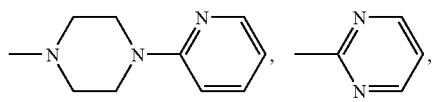

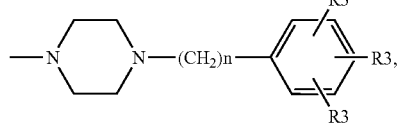

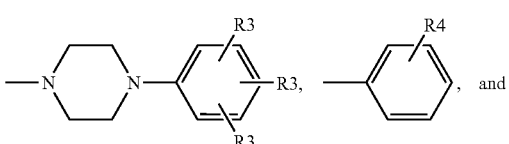

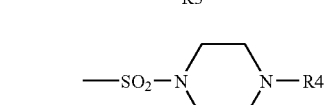

wherein $R_3$ is a member selected from the group of halogen, hydroxyl group, a saturated straight chain alkyl group of 1-3 carbon atoms and a hydrogen atom.

It is another object of the present invention to provide a second embodiment of a process for the preparation of a compound of formula II which comprises steps of (a) reacting of a compound of formula III

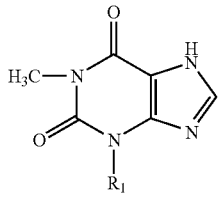

III with 1,2-di-bromoethane to produce a monobromo compound of formula IV according to the reaction a

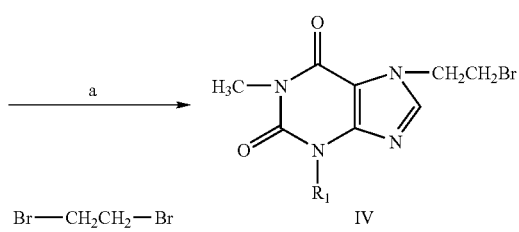

and (b) reacting said monobromo compound of formula IV with piperazine according to the reaction c to produce a compound of formula V wherein the N is not substituted,

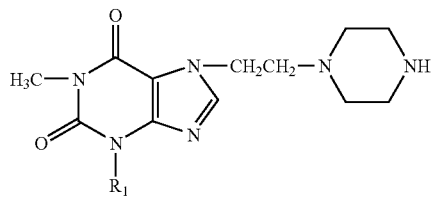

V and (c) reacting said compound of formula V according to the reaction d with a compound of formula R2-X to produce a compound of formula II,

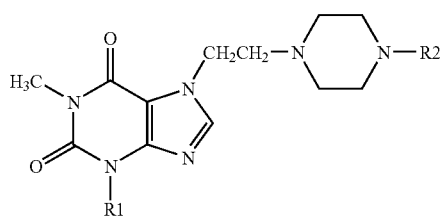

II wherein $R_1$ is —$(CH_2)cCH_3$; $R_2$ is a member of the group selected from the group of:

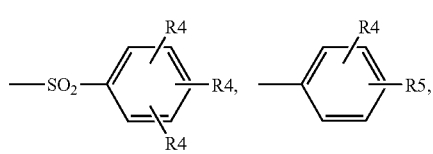

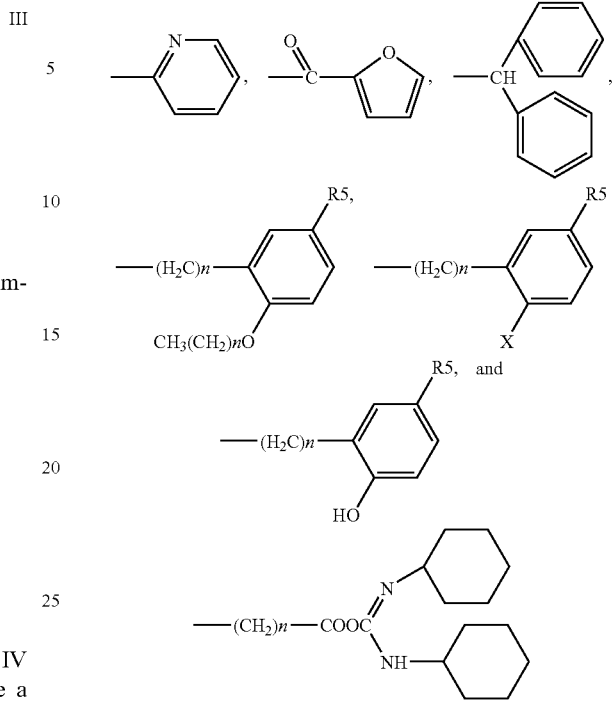

wherein $R_4$ is a member selected from the group of H, —$(CH_2)_nCH_3$, X, —$NH_2$, and —$NO_2$, wherein X is selected from the group of F, Cl, Br, or I, c is an integer from 0 to 3;
n is an integer from 0 to 3;
$R_5$ is a member selected from H, and the group of

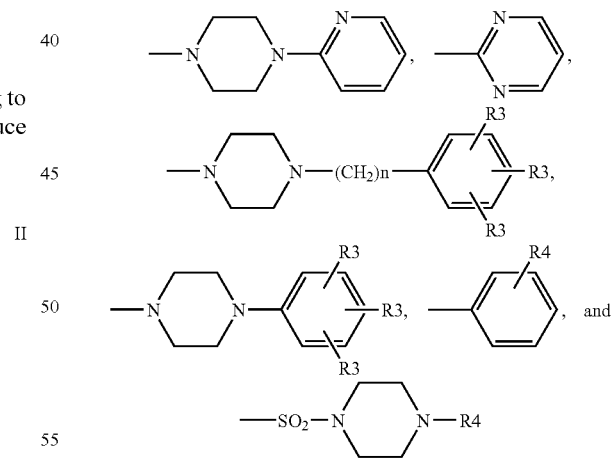

wherein $R_3$ is a member selected from the group of halogen, hydroxyl group, a saturated straight chain alkyl group of 1-3 carbon atoms and a hydrogen atom.

The purpose of the foregoing Abstract is to enable the United States patent and Trademark Office and the public generally, and especially the scientists, engineers, and practitioners in the art who are not familiar with patent or legal terms or phraseology, to determine quickly from a cursory inspection, the nature and essence of the technical disclosure of the application. The Abstract is neither intended to define the invention of the application, which is measured by the claims, nor is it intended to be limiting as to the scope of the invention in any way.

Still other objects and advantages of the present invention will become readily apparent to those skilled in this art from the following detailed description wherein I have shown and described only the preferred embodiment of the invention, simply by way of illustration of the best mode contemplated by carrying out my invention. As will be realized, the invention is capable of modification in various obvious respects all without departing from the invention. Accordingly, the drawings and description of the preferred embodiment are to be regarded as illustrative in nature, and not as restrictive in nature.

DESCRIPTION OF THE PREFERRED EMBODIMENTS

Figure 1:
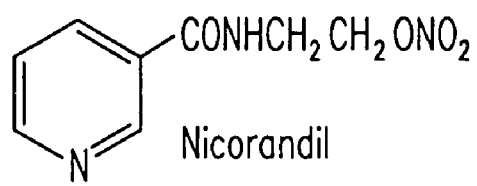
FIG. 1 illustrates a chemical structure of Nicorandil and Glibenclamide.
Figure 1:
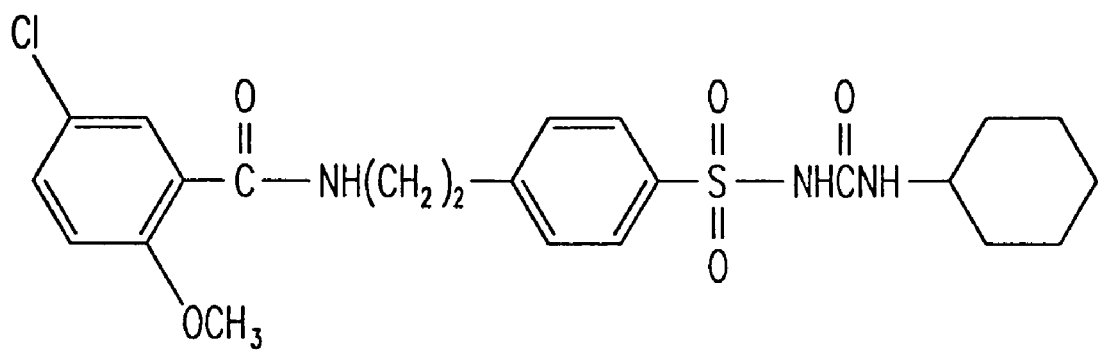

While the invention is susceptible of various modifications and alternative constructions, certain illustrated embodiments thereof have been shown in the drawings and will be described below in detail. It should be understood, however, that there is no intention to limit the invention to the specific form disclosed, but, on the contrary, the invention is to cover all modifications, alternative constructions, and equivalents falling within the spirit and scope of the invention as defined in the claims.

The compounds and a variety of other compounds of formulas I and II of the present invention may be formed and utilized within the scope of the present invention. The following Tables 1 and 2 set forth various compounds of formulas I and II which are considered a part of the present invention.

TABLE 1

Compounds of Formulas I and II

Formula II

| Compound No | $R_1$ | $R_2$ | $R_3$ | $R_4$ | $R_5$ | n |
|---|---|---|---|---|---|---|
| 1 | CH$_3$ | 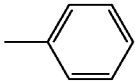 | — | H | H | 0 |
| 2 | —CH$_3$ | 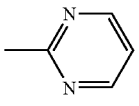 | — | — | — | 0 |
| 3 | —CH$_3$ | 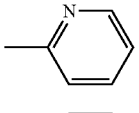 | — | — | — | 0 |
| 4 | —CH$_3$ | 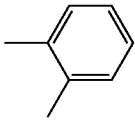 | — | —Cl on 2 | H | 0 |
| 5 | —CH$_3$ | 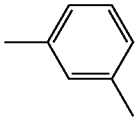 | — | —Cl on 3 | H | 0 |
| 6 | —CH$_3$ | 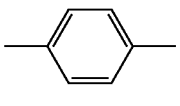 | — | —Cl on 4 | H | 0 |
| 7 | —CH$_3$ | 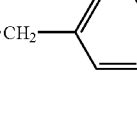 | — | H | H | 1 |

TABLE 1-continued

Compounds of Formulas I and II

| 8 | —CH₃ | (2-furoyl: —C(=O)-furan) | — | — | — | 0 |

Formula II

| Compound No. | $R_1$ | $R_2$ | $R_3$ | $R_4$ | $R_5$ |
|---|---|---|---|---|---|
| 9 | —CH₃ | 1,4-phenylene | — | —NO₂ on 2 | H |
| 10 | —CH₃ | 1,2-phenylene | — | CH₃O— on 2 | H |
| 11 | —CH₂CH(CH₃)₂ | phenyl | — | H | H |
| 12 | —CH₂CH(CH₃)₂ | 2-pyrimidinyl | — | — | — |
| 13 | —CH₂CH(CH₃)₂ | 2-pyridinyl | — | — | — |
| 14 | —CH₂CH(CH₃)₂ | 1,2-phenylene | — | —Cl on 2 | H |
| 15 | —CH₂CH(CH₃)₂ | 1,3-phenylene | — | —Cl on 5 | H |
| 16 | —CH₂CH(CH₃)₂ | 1,4-phenylene | — | —Cl on 4 | H |

| Compound No | $R_1$ | $R_2$ | $R_3$ | $R_4$ | $R_5$ | n |
|---|---|---|---|---|---|---|
| 17 | —CH₂CH(CH₃)₂ | —CH₂-phenyl | — | H | H | 1 |
| 18 | —CH₂CH(CH₃)₂ | 2-furoyl (—C(=O)-furan) | — | — | — | 0 |
| 19 | —CH₂CH(CH₃)₂ | 1,4-phenylene | — | —NO₂ on 4 | H | 0 |

TABLE 1-continued
Compounds of Formulas I and II
| No. | R₁ | R₂ | R₃ | R₄ | R₅ | n |
|---|---|---|---|---|---|---|
| 20 | —CH₂CH(CH₃)₂ | 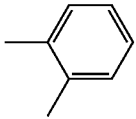 | — | CH₃O— on 2 | H | 0 |
| 21 | —CH₃ | 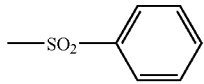 | — | — | — | 0 |
| 22 | —CH₃ | 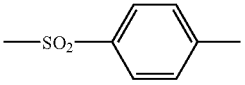 | — | CH₃O— on 4 | — | 0 |
| 23 | —CH₃ | 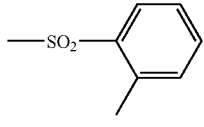 | — | CH₃O— on 2 | — | 0 |
| Compound No. | R₁ | R₂ | R₃ | R₄ | R₅ |
|---|---|---|---|---|---|
| 24 | —CH₂CH(CH₃)₂ | 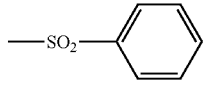 | — | — | — |
| 25 | —CH₂CH(CH₃)₂ | 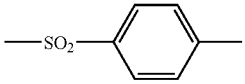 | — | —CH₃ on 4 | — |
| 26 | —CH₂CH(CH₃)₂ | 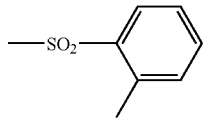 | — | —CH₃ on 2 | — |
Formula I
| Compound No | R₁ | R₂ | R₃ | R₄ | R₅ | n |
|---|---|---|---|---|---|---|
| 27 | —CH₃ | 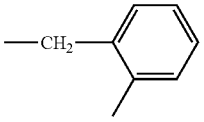 | — | —OH on 2 | H | 0 |
| 28 | —CH₃ | 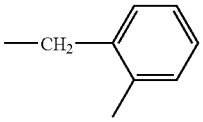 | — | C₂H₅O— on 2 | H | 1 |
| 29 | —CH₃ | 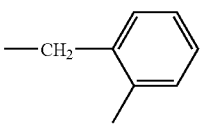 | — | C₃H₇O— on 2 | H | 2 |
| 30 | —CH₃ | 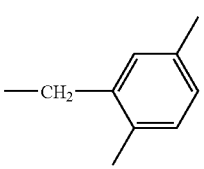 | — | HO— on 6 | CONH₂ on 3 | 0 |

TABLE 1-continued

Compounds of Formulas I and II

| | | | | | | |
|---|---|---|---|---|---|---|
| 31 | —CH$_3$ | —CH$_2$-(dimethylphenyl) | — | C$_2$H$_5$O— on 6 | CONH$_2$ on 3 | 1 |
| 32 | —CH$_3$ | —CH$_2$-(dimethylphenyl) | — | C$_3$H$_7$O— on 6 | CONH$_2$ on 3 | 2 |
| 33 | —CH$_3$ | —CH$_2$-(dimethylphenyl) | —CH$_3$ on 4 | —OH on 2 | —SO$_2$—N-piperazine-N— | 0 |
| 34 | —CH$_3$ | —CH$_2$-(dimethylphenyl) | —CH$_3$ on 4 | C$_2$H$_5$O— on 2, | —SO$_2$—N-piperazine-N— | 1 |
| 35 | —CH$_3$ | —CH$_2$-(dimethylphenyl) | —CH$_3$ on 4 | C$_3$H$_7$O— on 6 | —SO$_2$—N-piperazine-N— | 2 |
| 36 | —CH$_2$CH(CH$_3$)$_2$ | —CH$_2$-(dimethylphenyl) | — | —OH on 6 | H | 0 |
| 37 | —CH$_2$CH(CH$_3$)$_2$ | —CH$_2$-(dimethylphenyl) | — | C$_2$H$_5$O— on 6 | H | 1 |
| 38 | —CH$_2$CH(CH$_3$)$_2$ | —CH$_2$-(dimethylphenyl) | — | C$_3$H$_7$O— on 6 | H | 2 |
| 39 | —CH$_2$CH(CH$_3$)$_2$ | —CH$_2$-(dimethylphenyl) | — | —OH on 6 | —CONH$_2$ on 3 | 0 |

TABLE 1-continued

Compounds of Formulas I and II

| | | | | | | |
|---|---|---|---|---|---|---|
| 40 | —CH$_2$CH(CH$_3$)$_2$ | 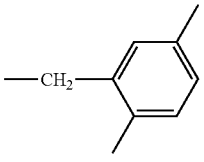 | — | C$_2$H$_5$O— on 6 | —CONH$_2$ on 3 | 1 |
| 41 | —CH$_2$CH(CH$_3$)$_2$ | 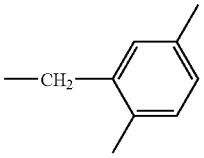 | — | C$_3$H$_7$O— on 6 | —CONH$_2$ on 3 | 1 |
| 42 | —CH$_2$CH(CH$_3$)$_2$ | 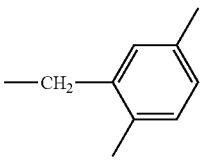 | —CH$_3$ on 4 | —OH on 2 | —SO$_2$—N⌒N— | 0 |
| 43 | —CH$_2$CH(CH$_3$)$_2$ | 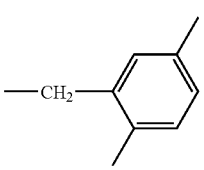 | —CH$_3$ on 4 | C$_2$H$_5$O— on 2, | —SO$_2$—N⌒N— | 1 |
| 44 | —CH$_2$CH(CH$_3$)$_2$ | 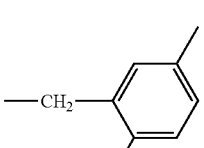 | —CH$_3$ on 4 | C$_3$H$_7$O— on 6 | —SO$_2$—N⌒N— | 2 |

TABLE 2

Chemical Names

| Compound No. | IUPAC-Name |
|---|---|
| 1 | 7-{2-[4-phenylpiperazinyl]ethyl}-1,3-dimethylxanthine |
| 2 | 7-{2-[4-(2-Pyrimidyl)piperazinyl]ethyl}-1,3-dimethylxanthine |
| 3 | 7-{2-[4-(2-Pyridyl)piperazinyl]ethyl}-1,3-dimethylxanthine |
| 4 | 7-{2-[4-(2-chlorophenyl)piperazinyl]ethyl}-1,3-dimethylxanthine |
| 5 | 7-{2-[4-(3-chlorophenyl)piperazinyl]ethyl}-1,3-dimethylxanthine |
| 6 | 7-{2-[4-(4-chlorophenyl)piperazinyl]ethyl}-1,3-dimethylxanthine |
| 7 | 7-{2-[4-benzylpiperazinyl]ethyl}-1,3-dimethylxanthine |
| 8 | 7-{2-[4-(2-furoyl)piperazinyl]ethyl}-1,3-dimethylxanthine |
| 9 | 7-{2-[4-(nitrobenzene)piperazinyl]ethyl}-1,3-dimethylxanthine |
| 10 | 7-{2-[4-(o-Methoxyphenyl)piperazinyl]ethyl}-1,3-dimethylxanthine |
| 11 | 7-{2-[4-phenylpiperazinyl]ethyl}-3-isobutyl-1-methylxanthine |
| 12 | 7-{2-[4-(2-Pyrimidyl)piperazinyl]ethyl}-3-isobutyl-1-methylxanthine |
| 13 | 7-{2-[4-(2-Pyridyl)piperazinyl]ethyl}-3-isobutyl-1-methylxanthine |
| 14 | 7-{2-[4-(2-chlorophenyl)piperazinyl]ethyl}-3-isobutyl-1-methylxanthine |
| 15 | 7-{2-[4-(3-chlorophenyl)piperazinyl]ethyl}-3-isobutyl-1-methylxanthine |
| 16 | 7-{2-[4-(4-chlorophenyl)piperazinyl]ethyl}-3-isobutyl-1-methylxanthine |
| 17 | 7-{2-[4-benzylpiperazinyl]ethyl}-3-isobutyl-1-methylxanthine |
| 18 | 7-{2-[4-(2-furoyl)piperazinyl]ethyl}-3-isobutyl-1-methylxanthine |
| 19 | 7-{2-[4-(nitrobenzene)piperazinyl]ethyl}-3-isobutyl-1-methylxanthine |
| 20 | 7-{2-[4-(o-Methoxyphenyl)piperazinyl]ethyl}-3-isobutyl-1-methylxanthine |
| 21 | 7-{2-[4-(phenylsulfonyl)piperazinyl]ethyl}-1,3-dimethylxanthine |
| 22 | 7-(2-{4-[(4-methylphenyl)sulfonyl]piperazinyl}ethyl)-1,3-dimethylxanthine |
| 23 | 7-{2-{4-[(2-methylphenyl)sulfonyl]piperazinyl}ethyl)-1,3-dimethylxanthine |
| 24 | 7-{2-[4-(phenylsulfonyl)piperazinyl]ethyl}-3-isobutyl-1-methylxanthine |
| 25 | 7-(2-{4-[(4-methylphenyl)sulfonyl]piperazinyl}ethyl)-3-isobutyl-1-methylxanthine |
| 26 | 7-(2-{4-[(2-methylphenyl)sulfonyl]piperazinyl}ethyl)-3-isobutyl-1-methylxanthine |

TABLE 2-continued

Chemical Names

| Compound No. | IUPAC-Name |
|---|---|
| 27 | 7-{2-[(2-hydroxybenzyl)amino]ethyl}-1,3-dimethylxanthine |
| 28 | 7-{2-[(2-ethoxybenzyl)amino]ethyl}-1,3-dimethylxanthine |
| 29 | 7-{2-[(2-propoxybenzyl)amino]ethyl}-1,3-dimethylxanthine |
| 30 | 3-({[2-(1,3-dimethyl-2,6-dioxo-1,2,3,6-tetrahydro-7H-purin-7-yl)ethyl]amino}methyl hydroxybenzamide |
| 31 | 3-({[2-(1,3-dimethyl-2,6-dioxo-1,2,3,6-tetrahydro-7H-purin-7-yl)ethyl]amino}methyl ethoxybenzamide |
| 32 | 3-({[2-(1,3-dimethyl-2,6-dioxo-1,2,3,6-tetrahydro-7H-purin-7-yl)ethyl]amino}methyl propoxybenzamide |
| 33 | 7-[2-({2-hydroxy-5-[(4-methylpiperazin-1-yl)sulfonyl]benzyl}amino)ethyl] dimethylxanthine |
| 34 | 7-[2-({5-[(4-methylpiperazin-1-yl)sulfonyl]-2-ethoxybenzyl}amino)ethyl] dimethylxanthine |
| 35 | 7-[12-({5-[(4-methylpiperazin-1-yl)sulfonyl]-2-propoxybenzyl}amino)ethyl] dimethylxanthine |
| 36 | 7-{2-[(2-hydroxybenzyl)amino]ethyl}-3-isobutyl-1-methylxanthine |
| 37 | 7-{2-[(2-ethoxybenzyl)amino]ethyl}-3-isobutyl-1-methylxanthine |
| 38 | 7-{2-[(2-propoxybenzyl)aniino]ethyl}-3-isobutyl-1-methylxanthine |
| 39 | 4-hydroxy-3-({[2-(3-isobutyl-1-methyl-2,6-dioxo-1,2,3,6-tetrahydro-7H-purin-7-yl)ethyl]amino}methyl)benzamide |
| 40 | 4-ethoxy-3-({[2-(3-isobutyl-1-methyl-2,6-dioxo-1,2,3,6-tetrahydro-7H-purin-7-yl)ethyl]amino}methyl)benzamide |
| 41 | 4-propoxy-3-({[2-(3-isobutyl-1-methyl-2,6-dioxo-1,2,3,6-tetrahydro-7H-purin-7-yl)ethyl]amino}methyl)benzamide |
| 42 | 7-[2-({2-hydroxy-5-[(4-methylpiperazin-1-yl)sulfonyl]benzyl}amino)ethyl]-3-isobutyl methylxanthine |
| 43 | 7-[2-({5-[(4-methylpiperazin-1-yl)sulfonyl]-2-ethoxybenzyl}amino)ethyl]-3-isobutyl methylxanthine |
| 44 | 7-[2-({5-[(4-methylpiperazin-1-yl)sulfonyl]-2-propoxybenzyl}amino)ethyl]-3-isobutyl methylxanthine |

Figure 4A:
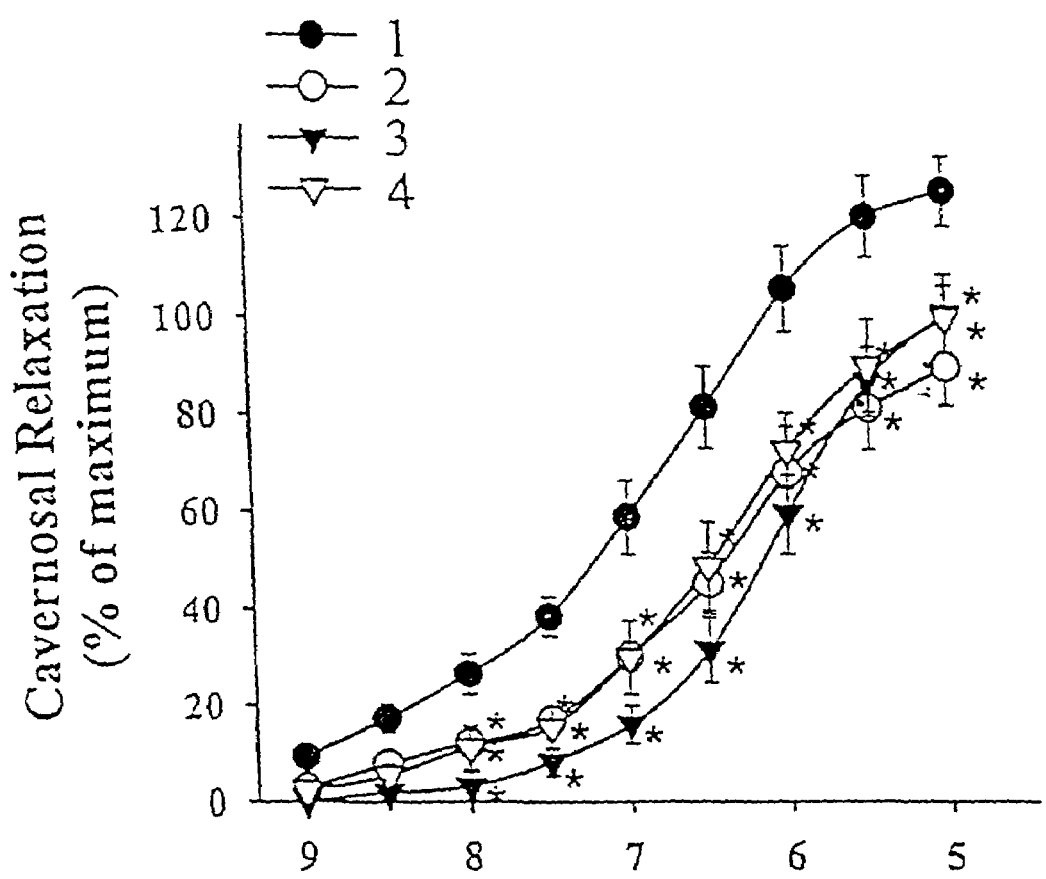
FIG. 4A shows a plot of Log [KMUP-1] v. cavernosal relaxation curves for illustrating the effects of a compound according to the present invention on phenylphrine precontracted rabbit corpus cavernosal in the absence and presence of L-NAME, methylene blue, ODQ.
Figure 4B:
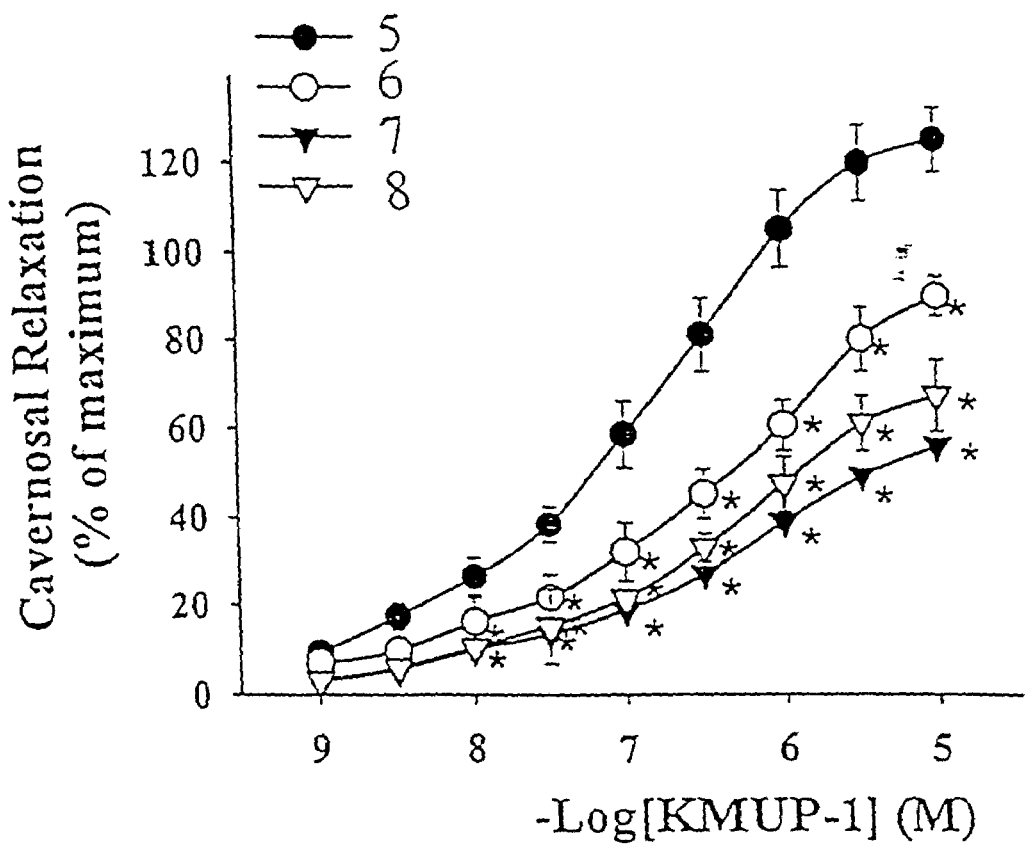
FIG. 4B shows a plot of Log [KMUP-1] v. cavernosal relaxation curves for illustrating the effects of a compound according to the present invention on phenylphrine precontracted rabbit corpus cavernosal in absence and presence of potassium channel blockers.
Figure 5:
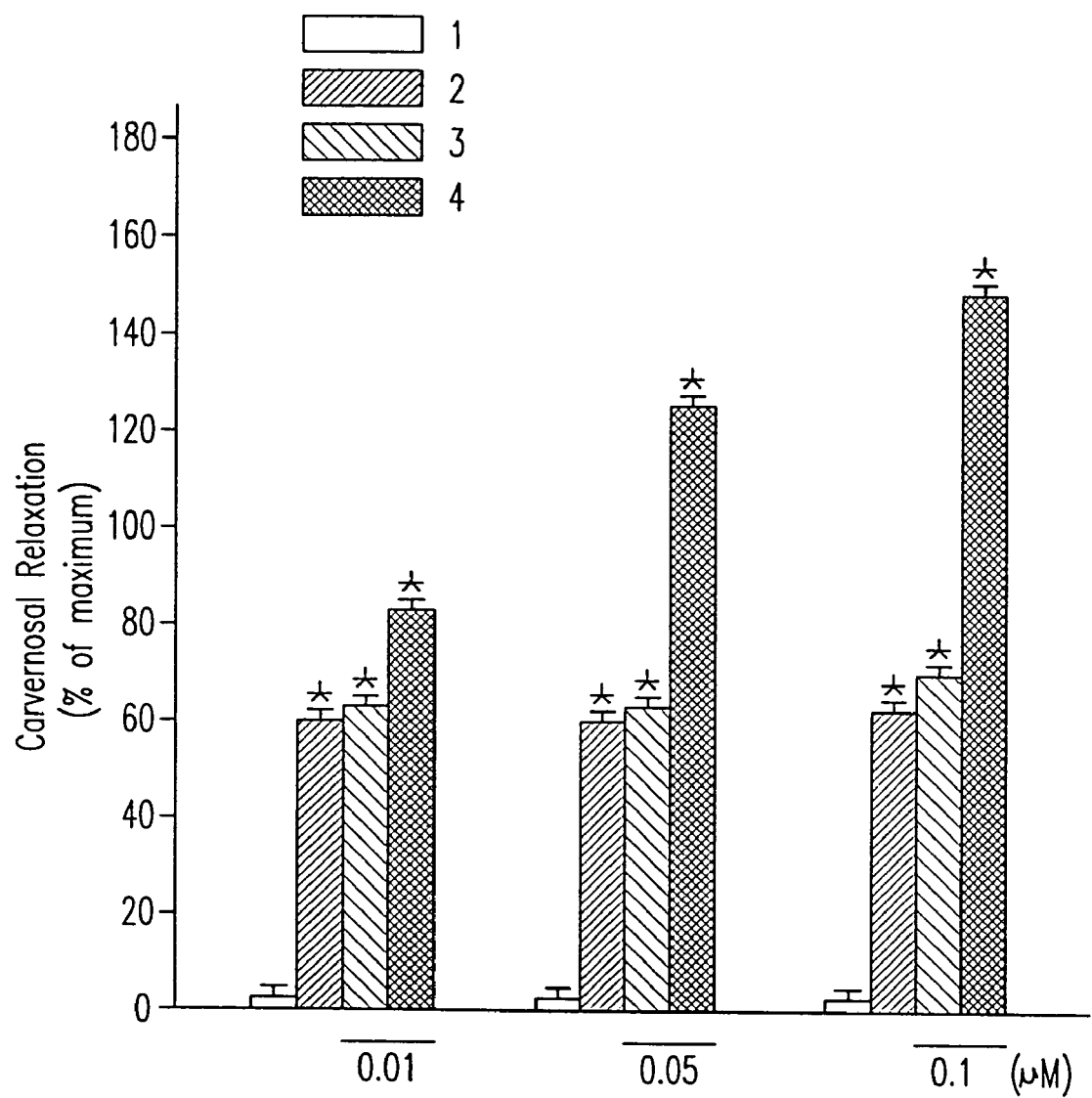
FIG. 5 shows a plot of dosage v. carvernosal relaxation illustrating the additive effects of a compound according to the present invention and IBMX (3-isobutyl-1-methylxanthine) on phenylephrine precontracted rabbit carvernosal strips.

The compounds of the present invention have been shown to provide various smooth muscle relaxant activities. Recently some reports have stated that theophyllline has an adenosine acceptor antagonist and phosphodiesterase (PDE) inhibitor function. Some of these derivatives of the present invention have been demonstrated to function as tracheal relaxation activity mechanism and provide for reduced heart rate functions. Some synthesized xanthine derivatives were observed to have their affinity and selective effect on adenosine $A_1$ and $A_2$ receptors. FIG. 4A illustrates the experimental results and the effects of compound 14 on phenylphrine precontracted rabbit corpus cavemosal in the absence and presence of L-NAME, methylene blue, ODQ. FIG. 4B illustrates the experimental results and the effects of compound 14 on phenylphrine precontracted rabbit corpus cavernosal in absence and presence of potassium channel blockers. FIG. 5 illustrates the additive effects of compound 14 and IBMX (3-isobutyl-1-methylxanthine) on phenylephrine precontracted rabbit carvernosal strips.

Figure 2:
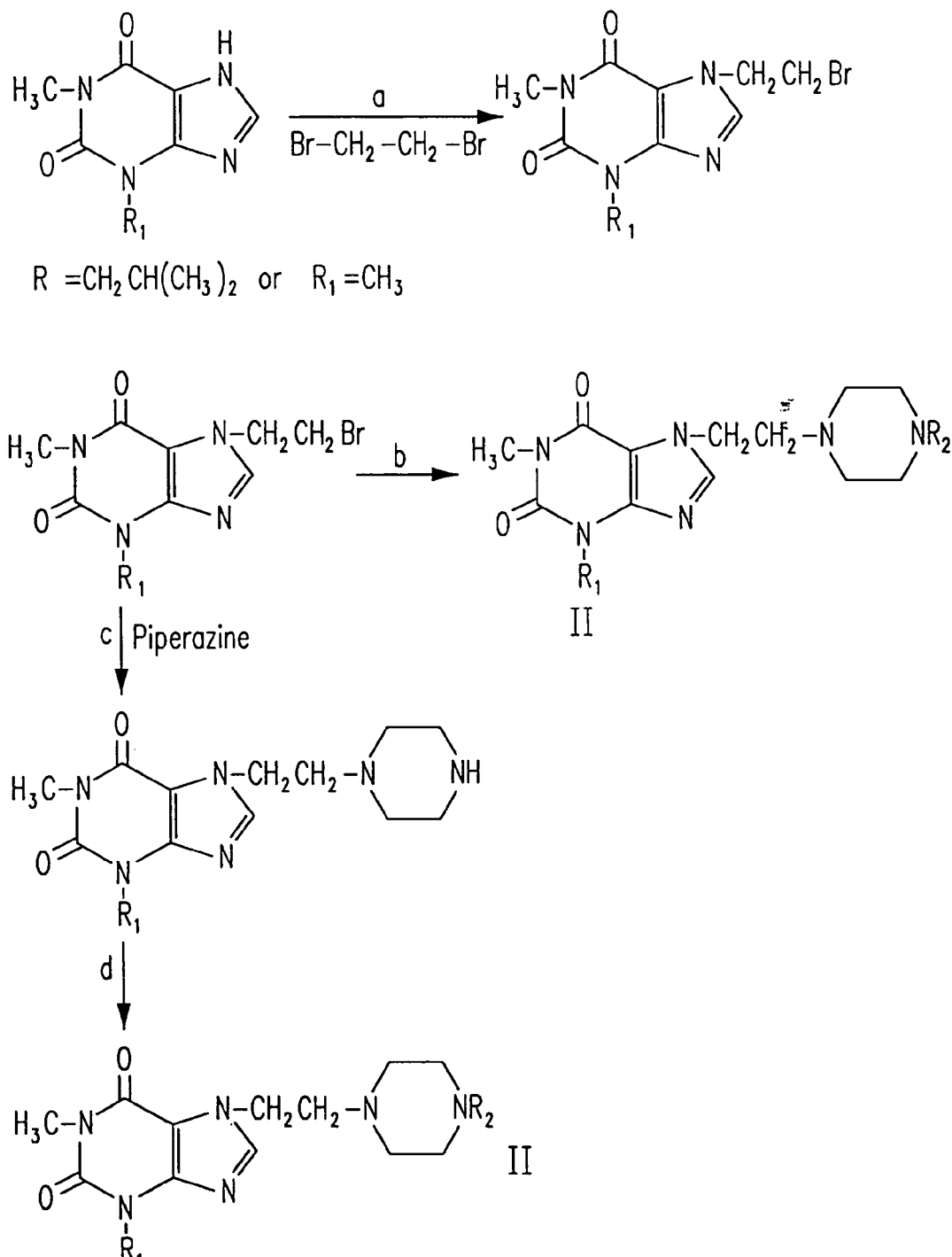
FIG. 2 illustrates the synthetic processes of the compounds of formula II according to the present invention.

Please refer to FIG. 2 in which two embodiments of processes for the preparation of a compound of formula II are disclosed. In a reaction a, the reactant of a compound of formula III is reacted with 1-2-di-bromoethane to produce a monobromo compound of formula IV. Then, in a first embodiment of the processes, by a reaction b, the monobromo compound of formula IV is reacted with an N-substituted piperazine of formula piperazinyl-R2 to produce a compound of formula II.

In a second embodiment of the processes, after the reaction a is carried out to obtain the monobromo compound of formula IV, the monobromo compound of formula IV is reacted with piperazine according to a reaction c to produce a compound of formula V. Then, the compound of formula is reacted with a compound of formula R2-X to produce a compound of formula II according to a reaction d.

Figure 3:
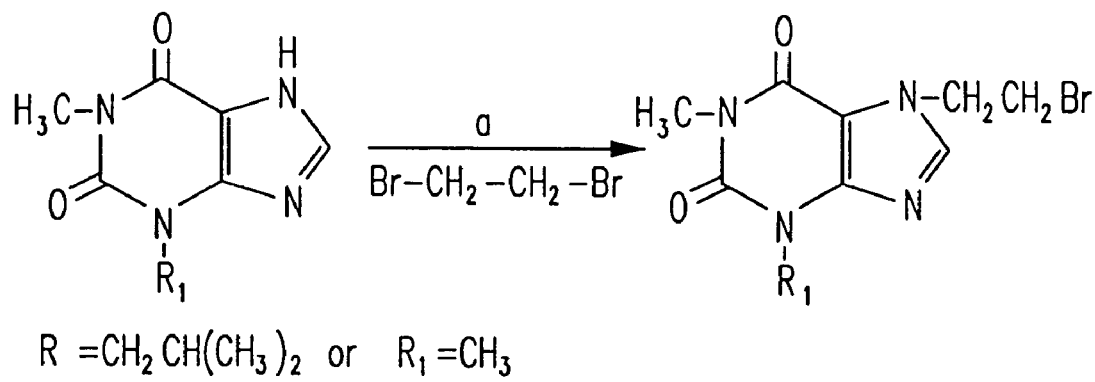
FIG. 3 illustrates the synthetic processes of the compounds of formula I according to the present invention.
Figure 3:
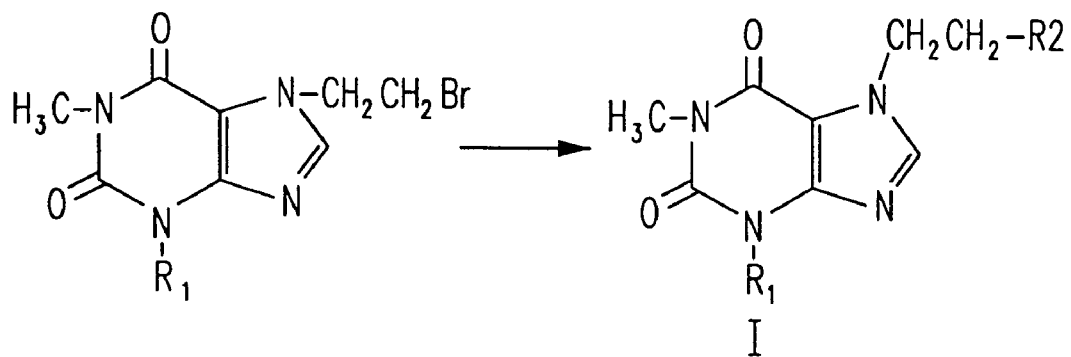

Please refer to FIG. 3. The compound of formula III is reacted with 1,2-di-bromoethane as shown in the reaction a to produce a monobromo compound of formula IV. Then, the monobromo compound of formula IV is reacted with piperazinyl ring which is a secondary amine, and NaOH is added to precipitate NaBr to obtain the product which contains the piperazinyl ring of formula I.

The compounds shown in FIGS. 2 and 3 have their main structures shown as Formulas I and II. In these compounds, various substitutions of the two bases lead to changes in the various intermediate products so that different serial preparing processes were developed. The preparing process for formula II, comprises the steps of dissolving 3-isobutyl-1methylxanthine (IBMX) into halogenated ethylamine solution, for example 2-bromoethylamine solution and stirring while heating the mixture until the solid is completely dissolved. Then NaOH is added to react with this mixture at a temperature of less than 150° C. over night. This is then concentrated under a reduced pressure to obtain a white coarse crystal which was re-crystallized to obtain a compound D (N7-bromoethyl 3-isobutyl-1-methylxanthine) which appears as a white crystal powder.

Into a three neck round bottom flask equipped with a mechanical stirrer, a thermometer, and a reflux condenser, there were added 210 g of chlorosulfonic acid and 20 g of para-hydroxyl sulfonate sodium. This mixture is then heated and stirred at 65° to 67° C., and then poured onto crushed ice. The precipitate is then separated by filtration. The precipitate is then washed with cold water and dried at 20-25 degrees C. under a reduced pressure. The precipitate is then purified by dissolution in 200 ml of acetone and precipitated again in cold distilled water, then filtered and dried in vacuum. This precipitate is then reacted with 10 ml of methylpiperazine for 1 hours to obtain a precipitate. This precipitate is then recrystallized in acetone to obtain a white crystal. This is then dissolved in a mixture of methanol, formalin (5 ml 37%), acetic acid 1 ml, and 10 g compound D (N7-bromoethyl 3-isobutyl-1-methyl-xanthine), then followed by mixing overnight at 75 degrees C., purification by column chromatography and eluted by a solvent system containing ethyl acetate and methanol. The eluate is then recrystallized from methanol to obtain compound 39. This compound 39 is dissolved in 50 ml methanol together with 1 g NaOH and 10 ml ethyl bromide, heated at 75 C for 2 hours and concentrated under a reduced pressure, dissolved and recrystallized in 50 ml methanol to obtain compound 40.

Under the same rule, compound 41 can be obtained by replacing ethyl bromide with propyl bromide. Compound 42, 43 or 44 were also obtained when replacing theophylline with IBMX, separately.

Parahydroxybenzoic acid ethyl ester is dissolved in methanol, added with formalin and acetic acid to react overnight, added to $NH_3$(aq) to obtain para-hydroxy benzoic amide. This product was added with formalin, acetic acid and N7-bromoethyl 3-isobutyl-1-methylxanthine processed through a Mannich reaction to obtain compound 33. Through purification and then dissolution into methanol, add NaOH and ethyl bromide to gain compound 34. Various substitutions can be made to produce other desired compounds. For example, by replacing ethyl bromide with propyl bromide, compound 35 can be obtained. By replacing theophylline with IBMX, compounds 36, 37, and/or 38 can be obtained.

The process of preparing the compound of formula I comprises the steps of dissolving 3-isobutyl-1-methylxanthine (IBMX) into methanol and stirring with 2-bromoethylamine upon a mantle heater, reacting this mixture with NaOH and then recrystallizing this mixture with methanol to obtain N7-bromoehtyl 3-isobutyl-1-methylxanthine.

To produce the serial compounds 1-8, which have different substitutes on a major structure, the preparing methods are as follows: refluxing compound A with methanol and added with one of the following compounds: 1-phenylpiperazine, 1-(2-pyrimidyl)piperazine, 1-(2-pyridyl)piperazine, 1-(2-chlorophenyl)piperazine, and 1-(4-chlorophenyl)piperazine. Compounds 11~18 were obtained by substituting the theophylline base with IBMX.

A solution of benzenesulfonyl chloride, piperazine and methanol allows us to obtain benzenesulfonyl piperazine. This product is dissolved into methanol and replaced with compound A (N-7-bromoethyl 3-isobutyl-1-methylxanthine) to obtain compound 21. By replacing the ethyl bromide with propyl bromide, compounds 22 and 23 can be produced. By replacing p-toluene-sulfonyl chloride or o-toluenesulfonyl chloride with benzenesulfonyl chloride, compounds 24, 25, or 26 may be produced.

Dissolving theophylline with methanol, added with 1,2-dibromoethane and NaOH, heated under reflux conditions, concentrated under a reduced pressure and purified through silica gel column chromatography, we can obtain compound A. Dissolving compound A into methanol and combining with piperazine, we can obtain compound B. Then steps of dissolving compound B in methanol, adding 2-furoyl chloride or 4-chloronitrobenzene and proceeding under reflux conditions allow for the formation of compounds 9 and 10.

Adding 4-chlorobenzene sulfonyl chloride and methylpiperazine into methanol and then refluxing, dissolving the product compound and N7-bromoethyl 3-isobutyl-1-methylxanthine in methanol, and then refluxing this solution, compound 45 is produced. According to the same rule, steps of replacing ethyl bromide with propyl bromide and replacing theophylline with IBMX allow the parties to obtain compound 46.

After purification and crystallization, the products are individually tested for their physio-chemical information including element analysis, MS, IR, H-NMR ($CDCl_3$), and UV etc as shown Table 3. Appropriate experimental models may also be utilized to evaluate their pharmacological activities, and examples of the experiments are shown in Tables 4-6 and in the following portions of the specification.

TABLE 3

The physicochemical Data of N7-substituted xanthines
Compound

| MS(SCAN FAB+) | $^1$H-NMR($CDCl_3$) | |
| --- | --- | --- |
| | Compound 4 | |
| 444.88 | δ: 0.94-0.98(d, 6H, 2×C$\underline{H}_3$), | 2.24-2.38(m, 1H, C$\underline{H}$), |
| | 2.70(t, 4H, 2×C$\underline{H}_2$), | 2.85(t, 2H, NC$\underline{H}_2$), |
| | 3.04(t, 4H, 2×C$\underline{H}_2$), | 3.42(s, 3H, NC$\underline{H}_3$), |
| | 3.93-3.96(d, 2H, C$\underline{H}_2$), | 4.45(t, 2H, NC$\underline{H}_2$), |
| | 6.97-7.01(m, 2H, 2×Ar—$\underline{H}$), | 7.27-7.36(m, 2H, 2×Ar—$\underline{H}$), |
| | 7.69(s, 1H, imidazole-$\underline{H}$) | |
| | Compound 14 | |
| 402.88 | δ: 2.70(t, 4H, 2×C$\underline{H}_2$), | 2.85(t, 2H, NC$\underline{H}_2$), |
| | 3.04(t, 4H, 2×C$\underline{H}_2$), | 3.42(s, 3H, NC$\underline{H}_3$), |
| | 3.60(s, 3H, NC$\underline{H}_3$), | 4.45(t, 2H, NC$\underline{H}_2$), |
| | 6.97-7.01(m, 2H, 2×Ar—$\underline{H}$), | 7.27-7.36(m, 2H, 2×Ar—$\underline{H}$), |
| | 7.69(s, 1H, imidazole-$\underline{H}$) | |
| | Compound 17 | |
| 398.46 | δ: 2.75(t, 4H, 2×C$\underline{H}_2$), | 2.89(t, 2H, NC$\underline{H}_2$), |
| | 3.09(t, 4H, 2×C$\underline{H}_2$), | 3.42(s, 3H, NC$\underline{H}_3$), |
| | 3.61(s, 3H, NC$\underline{H}_3$), | 3.86(s, 3H, OC$\underline{H}_3$), |
| | 4.49(t, 2H, NC$\underline{H}_2$), | 6.88-7.06(m, 4H, 4×Ar—$\underline{H}$), |
| | 7.72(s, 1H, imidazole-$\underline{H}$) | |

TABLE 3-continued

The physicochemical Data of N7-substituted xanthines
Compound

| MS(SCAN FAB+) | $^1$H-NMR(CDCl$_3$) |
|---|---|

Compound 22

488.38   δ: 0.94-0.98(d, 6H, 2×CH$_3$),    1.98(m, 3H, Ar—CH$_3$)
         2.24-2.38(m, 1H, CH),           2.70(t, 4H, 2×CH$_2$),
         2.85(t, 2H, NCH$_2$),            3.04(t, 4H, 2×CH$_2$),
         3.42(s, 3H, NCH$_3$),            3.93-3.96(d, 2H, CH$_2$),
         4.45(t, 2H, NCH$_2$),            6.97-7.01(m, 2H, 2×Ar—H),
         7.27-7.36(m, 2H, 2×Ar—H),       7.69(s, 1H, imidazole-H), Compound 25

446.38   δ: 1.98(m, 3H, Ar—CH$_3$)       2.70(t, 4H, 2×CH$_2$),
         2.85(t, 2H, NCH$_2$),            3.04(t, 4H, 2×CH$_2$),
         3.42(s, 3H, NCH$_3$),            3.60(s, 3H, NCH$_3$),
         4.45(t, 2H, NCH$_2$),            6.97-7.01(m, 2H, 2×Ar—H),
         7.27-7.36(m, 2H, 2×Ar—H),       7.69(s, 1H, imidazole-H), Compound 34

392.14   δ: 0.94-0.98(d, 6H, 2×CH$_3$),   1.4(t, 2H, CH$_2$),
         2.24-2.38(m, 1H, CH)            2.28(s, 2H, CH$_2$),
         2.85(t, 2H, NCH$_2$)             3.42(s, 3H, NCH$_3$)
         3.93-3.96(d, 2H, CH$_2$),        4.13(t, 3H, CH$_3$)
         4.45(t, 2H, NCH$_2$),            6.97-7.01(m, 2H, 2×Ar—H)
         7.27-7.36(m, 1H, Ar—H),         7.69(s, 1H, imidazole-H),
         7.98(b, 1H, NH),                8.2(b, 2H, NH$_2$)

Compound 38

364.14   δ: 1.4(t, 2H, CH$_2$),           2.2(t, 2H, CH$_2$),
         2.28(s, 2H, CH$_2$),             2.85(t, 2H, NCH$_2$),
         3.42(s, 3H, NCH$_3$),            3.60(s, 3H, NCH$_3$),
         4.13(t, 3H, CH$_3$),             4.45(t, 2H, NCH$_2$),
         6.97-7.01(m, 2H, 2×Ar—H),       7.27-7.36(m, 1H, Ar—H),
         7.69(s, 1H, imidazole-H)        7.98(b, 1H, NH)
         8.2(b, 2H, NH$_2$)

Compound 40

511.14   δ: 0.94-0.98(d, 6H, 2×CH$_3$),   1.4(t, 2H, CH$_2$),
         1.98(m, 3H, Ar—CH$_3$),         2.24-2.38(m, 1H, CH),
         2.28(s, 2H, CH$_2$),             2.70(t, 4H, 2×CH$_2$),
         2.85(t, 2H, NCH$_2$),            3.04(t, 4H, 2×CH$_2$),
         3.42(s, 3H, NCH$_3$),            3.93-3.96(d, 2H, CH$_2$),
         4.13(t, 3H, CH$_3$),             4.45(t, 2H, NCH$_2$),
         6.97-7.01(m, 2H, 2×Ar—H),       7.27-7.36(m, 1H, Ar—H),
         7.69(s, 1H, imidazole-H),       7.98(b, 1H, NH)

Compound 44

483.14   δ: 1.4(t, 2H, CH$_2$),           1.8(t, 2H, CH$_2$),
         1.98(m, 3H, Ar—CH$_3$),         2.28(s, 2H, CH$_2$),
         2.70(t, 4H, 2×H$_2$),            2.85(t, 2H, NCH$_2$),
         3.04(t, 4H, 2×CH$_2$),           3.42(s, 3H, NCH$_3$),
         3.60(s, 3H, NCH$_3$),            4.13(t, 3H, CH$_3$)
         4.45(t, 2H, NCH$_2$),            6.97-7.01(m, 2H, 2×Ar—H),
         7.27-7.36(m, 1H, Ar—H),         7.69(s, 1H, imidazole-H)
         7.98(b, 1H, NH), Compound 45

436.14   δ: 0.94-0.98(d, 6H, 2×CH$_3$),   1.98(m, 3H, Ar—CH$_3$),
         2.24-2.38(m, 1H, CH),           2.28(s, 2H, CH$_2$),
         2.70(t, 4H, 2×CH$_2$),           2.85(t, 2H, NCH$_2$),
         3.04(t, 4H, 2×CH$_2$),           3.42(s, 3H, NCH$_3$),
         3.93-3.96(d, 2H, CH$_2$),        4.13(t, 3H, CH$_3$),
         4.45(t, 2H, NCH$_2$),            6.97-7.01(m, 2H, 2×Ar—H),
         7.27-7.36(m, 1H, Ar—H),         7.69(s, 1H, imidazole-H),
         7.98(b, 1H, NH),

TABLE 4

Rabbit Corpus Cavernosal Relaxation $IC_{50}$

| compound | $PDE_5$ (human platelet) $IC_{50}$ (nM) | Rabbit Corpus Cavernosal Relaxation $IC_{50}$ |
|---|---|---|
| 4 | 3.9 ± 0.1 | 7.16 ± 0.09 |
| 7 | 4.2 ± 0.2 | 7.13 ± 0.06 |
| 14 | 3.8 ± 0.2 | 7.84 ± 0.08 |
| 17 | 6.2 ± 0.2 | 7.64 ± 0.07 |
| 23 | 5.2 ± 0.1 | 7.38 ± 0.04 |
| 26 | 4.8 ± 0.2 | 7.42 ± 0.09 |
| 34 | 0.4 ± 0.2 | 8.13 ± 0.05 |
| 37 | 0.3 ± 0.1 | 8.03 ± 0.04 |
| 35 | 0.4 ± 0.1 | 8.25 ± 0.06 |
| 38 | 0.6 ± 0.2 | 8.16 ± 0.07 |
| 39 | 0.6 ± 0.2 | 8.16 ± 0.07 |
| 42 | 0.6 ± 0.2 | 8.16 ± 0.07 |
| 40 | 0.6 ± 0.1 | 8.27 ± 0.04 |
| 43 | 0.7 ± 0.2 | 8.15 ± 0.06 |
| 41 | 0.8 ± 0.2 | 8.30 ± 0.07 |
| 44 | 0.9 ± 0.1 | 8.25 ± 0.08 |
| 45 | 0.6 ± 0.2 | 7.92 ± 0.07 |
| 46 | 5.2 ± 0.1 | 7.96 ± 0.03 |

TABLE 5

Rabbit Corpus Cavernosal Relaxation $IC_{50}$ on $K^+$ channels blocker

| Drug pretreatment | Dose | $-Log\ EC_{50}$ |
|---|---|---|
| Control | | 7.19 ± 0.09 |
| TEA | 10 mM | 5.037 ± 0.05 |
| Glibenclamide | 1 µM | 6.57 ± 0.15 |
| 4-AP | 100 µM | 5.83 ± 0.17 |
| L-NAME | 100 µM | 6.51 ± 0.08 |
| Methylene blue | 10 µM | 6.51 ± 0.06 |
| ODQ | 1 µM | 6.79 ± 0.12 |

TABLE 6

Peak increased intracavernous pressure (ΔICP) and duration of tumescence response to compounds at 2 mg/kg in rabbits

| compound | ΔICP (mmHg) | Duration (min) |
|---|---|---|
| Compound 10 | 12 ± 1.6 | 13 ± 2.1 |
| Compound 4 | 14 ± 2.1 | 14 ± 1.1 |
| Compound 9 | 25 ± 1.3 | 16 ± 1.2 |
| Compound 12 | 23 ± 1.5 | 15 ± 1.3 |
| Compound 18 | 26 ± 1.4 | 18 ± 1.3 |

The compound of this invention includes various carriers, diluents and pharmacologically approved salts to provide desired therapeutic efficacy. Such pharmaceutical preparation could be in solid form for oral or rectal administration, liquid form for non-intestinal injection or ointment form for direct application on an affected part. Such forms are manufactured according to common pharmaceutical preparation methods and combined with common carriers such as starch, glycerine, carboxy methylcellulose, lactose, magnesium and similar materials. The general dosage of the compound could be varied. However, a normal person could utilize 50 to 300 mg, approximately three times a day.

What is claimed is:

1. A compound containing the theophylline moiety of formula II

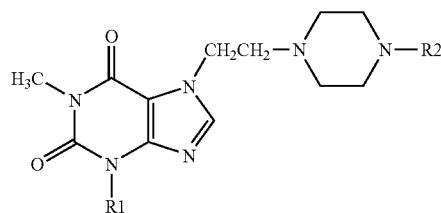

wherein $R_1$ is —$(CH_2)cCH_3$; $R_2$ is a member of the group selected from the group consisting of:

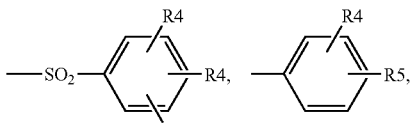

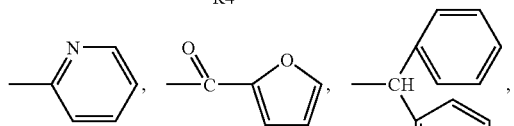

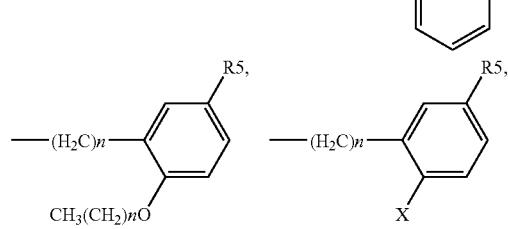

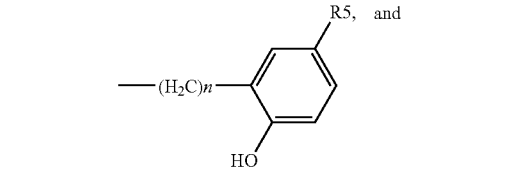

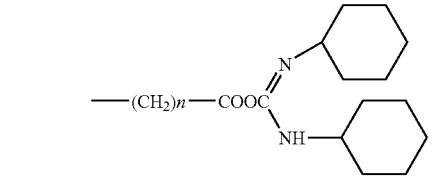

wherein
$R_4$ is a member selected from the group consisting of H, —$(CH_2)_nCH_3$, X, —$NH_2$, and —$NO_2$, wherein X is selected from the group consisting of F, Cl, Br, and I,
c is an integer from 0 to 3;
n is an integer from 0 to 3;
$R_5$ is a member selected from H, and the group consisting of

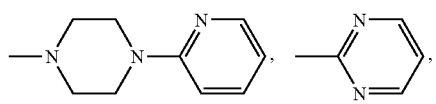

-continued

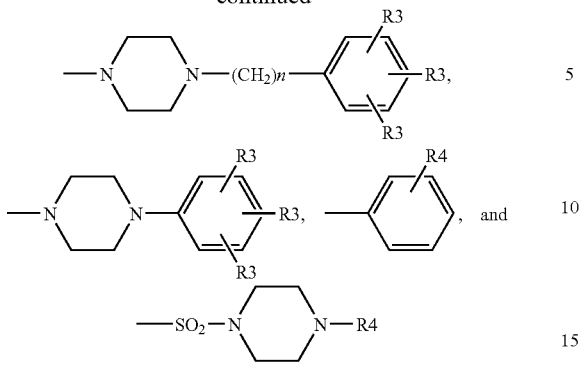

wherein $R_3$ is a member selected from the group consisting of halogen, hydroxyl group, a saturated straight chain alkyl group of 1-3 carbon atoms and a hydrogen atom.

2. A process for the preparation of a compound of formula II according to claim 1 which comprises steps of (a) reacting of a compound of formula III

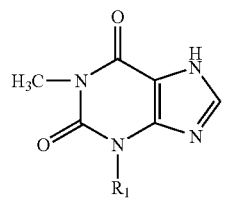

with 1,2-di-bromoethane to produce a monobromo compound of formula IV,

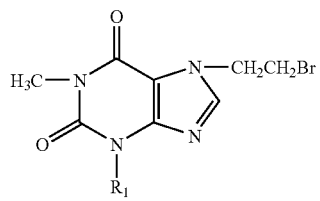

and (b) reacting said monobromo compound of formula IV with a N-substituted piperazine of formula piperazinyl-R2 to produce a compound of formula II.

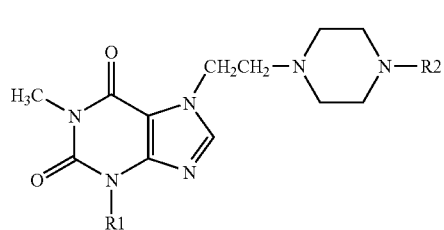

3. A process for the preparation of a compound of formula II according to claim 1 which comprises steps of (a) reacting of a compound of formula III,

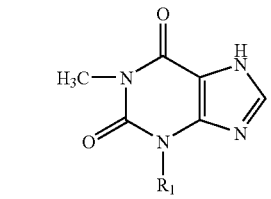

with 1,2-di-bromoethane to produce a monobromo compound of formula IV,

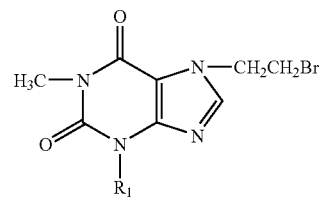

and (b) reacting said monobromo compound of formula IV with piperazine to produce a compound of formula V wherein the N is not substituted,

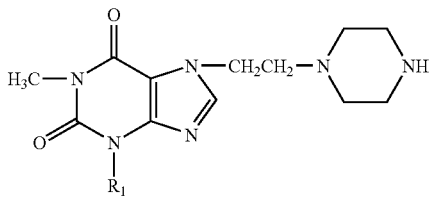

and (c) reacting said compound of formula V with a compound of formula R2-X to produce a compound of the following formula II:

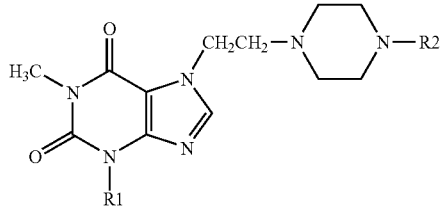

wherein $R_1$ is $-(CH_2)cCH_3$; $R_2$ is a member of the group selected from the group consisting of:

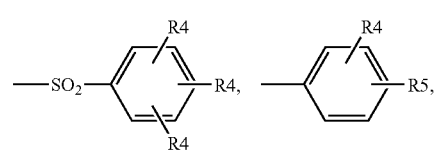

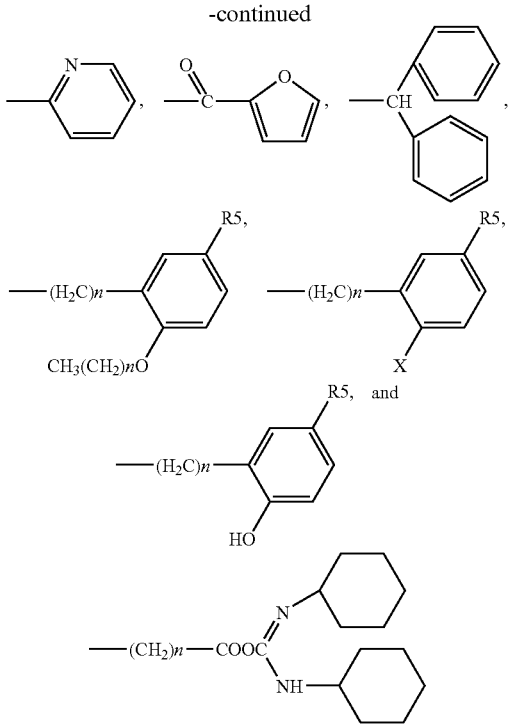

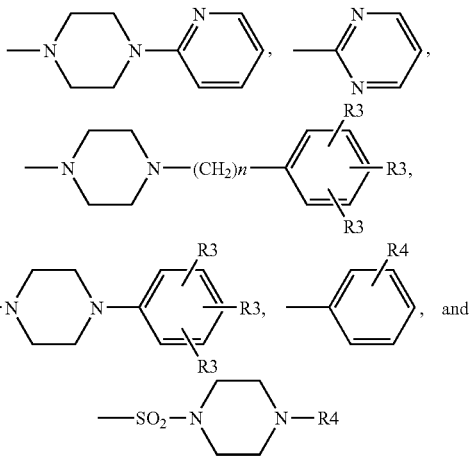

wherein
R$_4$ is a member selected from the group consisting of H, —(CH$_2$)$_n$CH$_3$, X, —NH$_2$, and —NO$_2$, wherein X is selected from the group consisting of F, Cl, Br, and I,
c is an integer from 0 to 3;
n is an integer from 0 to 3;

R$_5$ is a member selected from H, and the group consisting of:

wherein R$_3$ is a member selected from the group consisting of halogen, hydroxyl group, a saturated straight chain alkyl group of 1-3 carbon atoms and a hydrogen atom.

4. The process of claim 2 wherein R$_3$ is H, and n is between 1 and 3.

5. A pharmaceutical composition which has corpus cavernosal relaxation activity containing a compound defined in claim 1 together with a carrier.

6. The compound of claim 1 wherein R$_3$ is H, and n is between 1 and 3.

7. The process of claim 3 wherein R$_3$ is H, and n is between 1 and 3.

* * * * *